(12) United States Patent
Schelberger et al.

(10) Patent No.: US 6,503,936 B1
(45) Date of Patent: Jan. 7, 2003

(54) FUNGICIDAL MIXTURES

(75) Inventors: Klaus Schelberger, Gönnheim (DE); Maria Scherer, Landau (DE); Reinhold Saur, Böhl-Iggelheim (DE); Hubert Sauter, Mannheim (DE); Bernd Müller, Frankenthal (DE); Erich Birner, Altleiningen (DE); Joachim Leyendecker, Ladenburg (DE); Eberhard Ammermann, Heppenheim (DE); Gisela Lorenz, Neustadt (DE); Siegfried Strathmann, Limburgerhof (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/856,034

(22) PCT Filed: Nov. 6, 1999

(86) PCT No.: PCT/EP99/08512

§ 371 (c)(1),
(2), (4) Date: May 17, 2001

(87) PCT Pub. No.: WO00/30450

PCT Pub. Date: Jun. 2, 2000

(30) Foreign Application Priority Data

Nov. 19, 1998 (DE) .......................................... 198 53 503

(51) Int. Cl.$^7$ ........................ A01N 43/64; A01N 43/56; A01N 59/20; A01N 57/18; A01N 43/42
(52) U.S. Cl. ........................ 514/383; 424/630; 424/632; 424/633; 424/635; 424/637; 424/638; 514/161; 514/312; 514/407; 514/499
(58) Field of Search ................................. 514/407, 383, 514/312, 161, 499; 424/630, 632, 633, 635, 637, 638

(56) References Cited

FOREIGN PATENT DOCUMENTS

| EP | 741 970 | 11/1996 |
|----|---------|---------|
| WO | 96/03047 | 2/1996 |
| WO | 97/15189 | 5/1997 |
| WO | 98/41094 | 9/1998 |
| WO | 98/53693 | 12/1998 |

*Primary Examiner*—Allen J. Robinson
(74) *Attorney, Agent, or Firm*—Keil & Weinkauf

(57) ABSTRACT

A fungicidal mixture comprising
  a.1) a carbamate of the formula I.a,

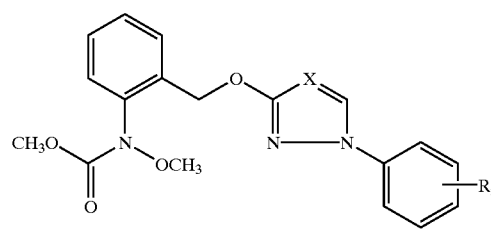

in which X is CH or N, n is 0, 1 or 2 and R is halogen, $C_1$–$C_4$-alkyl or $C_1$–$C_4$-haloalkyl, where the radicals R can be different if n is 2, and
b) a copper-containing fungicidal active compound (II) in a synergistically active amount.

9 Claims, No Drawings

FUNGICIDAL MIXTURES

This application is a 371 of PCT/EP99/08512, filed Nov. 6, 1999. The present invention relates to a fungicidal mixture which comprises a.1) a carbamate of the formula I.a,

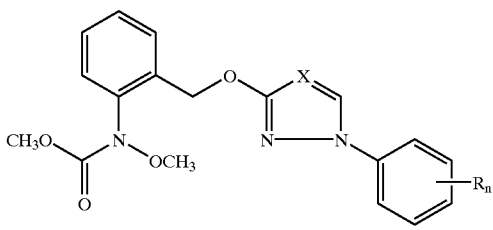

in which X is CH or N, n is 0, 1 or 2 and R is halogen, $C_1$–$C_4$-alkyl or $C_1$–$C_4$-haloalkyl, where the radicals R can be different if n is 2, and b) a copper-containing fungicidal active compound (II) in a synergistically active amount.

Moreover, the invention relates to processes for controlling harmful fungi using mixtures of the compounds I and II and the use of the compounds I and the compounds II for the production of mixtures of this type.

The compounds of the formula I, their preparation and their action against harmful fungi are disclosed in the literature (WO-A 96/01,256; WO-A 96/01,258).

The use of copper-containing compounds for controlling harmful fungi is likewise known.

With respect to the lowering of the application rates and an improvement in the spectrum of action of the known compounds I and II, the present invention is based on mixtures which have an improved action against harmful fungi together with a decreased total amount of applied active compounds (synergistic mixtures).

Accordingly, the mixture defined at the outset has been found. It has moreover been found that on simultaneous, to be precise, joint or separate application of the compound I and the compound II or on application of the compound I and the compound II in succession, harmful fungi can be controlled better than with the individual compounds on their own.

The formula I.a in particular represents carbamates in which the combination of the substituents corresponds to one line of the following Table:

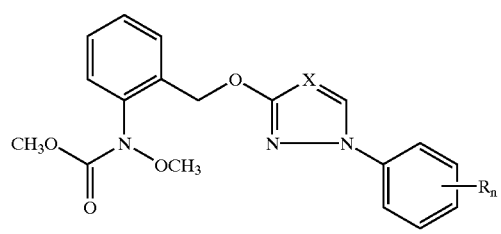

| No. | X | $R_n$ |
|---|---|---|
| I.1 | N | 2-F |
| I.2 | N | 3-F |
| I.3 | N | 4-F |
| I.4 | N | 2-Cl |
| I.5 | N | 3-Cl |
| I.6 | N | 4-Cl |
| I.7 | N | 2-Br |
| I.8 | N | 3-Br |
| I.9 | N | 4-Br |
| I.10 | N | 2-$CH_3$ |
| I.11 | N | 3-$CH_3$ |
| I.12 | N | 4-$CH_3$ |
| I.13 | N | 2-$CH_2CH_3$ |
| I.14 | N | 3-$CH_2CH_3$ |
| I.15 | N | 4-$CH_2CH_3$ |
| I.16 | N | 2-$CH(CH_3)_2$ |
| I.17 | N | 3-$CH(CH_3)_2$ |
| I.18 | N | 4-$CH(CH_3)_2$ |
| I.19 | N | 2-$CF_3$ |
| I.20 | N | 3-$CF_3$ |
| I.21 | N | 4-$CF_3$ |
| I.22 | N | 2,4-$F_2$ |
| I.23 | N | 2,4-$Cl_2$ |
| I.24 | N | 3,4-$Cl_2$ |
| I.25 | N | 2-Cl,4-$CH_3$ |
| I.26 | N | 3-Cl,4-$CH_3$ |
| I.27 | CH | 2-F |
| I.28 | CH | 3-F |
| I.29 | CH | 4-F |
| I.30 | CH | 2-Cl |
| I.31 | CH | 3-Cl |
| I.32 | CH | 4-Cl |
| I.33 | CH | 2-Br |
| I.34 | CH | 3-Br |
| I.35 | CH | 4-Br |
| I.36 | CH | 2-$CH_3$ |
| I.37 | CH | 3-$CH_3$ |
| I.38 | CH | 4-$CH_3$ |
| I.39 | CH | 2-$CH_2CH_3$ |
| I.40 | CH | 3-$CH_2CH_3$ |
| I.41 | CH | 4-$CH_2CH_3$ |
| I.42 | CH | 2-$CH(CH_3)_2$ |
| I.43 | CH | 3-$CH(CH_3)_2$ |
| I.44 | CH | 4-$CH(CH_3)_2$ |
| I.45 | CH | 2-$CF_3$ |
| I.46 | CH | 3-$CF_3$ |
| I.47 | CH | 4-$CF_3$ |
| I.48 | CH | 2,4-$F_2$ |
| I.49 | CH | 2,4-$Cl_2$ |
| I.50 | CH | 3,4-$Cl_2$ |
| I.51 | CH | 2-Cl,4-$CH_3$ |
| I.52 | CH | 3-Cl,4-$CH_3$ |

The compounds I.12, I.23, I.32 and I.38 are particularly preferred.

Because of the basic character of the nitrogen atoms contained in them, the compounds I are able to form salts or adducts with inorganic or organic acids or with metal ions.

Examples of inorganic acids are hydrohalic acids such as hydrofluoric acid, hydrochloric acid, hydrobromic acid and hydriodic acid, sulfuric acid, phosphoric acid and nitric acid.

Suitable organic acids are, for example, formic acid, carbonic acid and alkanoic acids such as acetic acid, trifluoroacetic acid, trichloroacetic acid and propionic acid as well as glycolic acid, thiocyanic acid, lactic acid, succinic acid, citric acid, benzoic acid, cinnamic acid, oxalic acid, alkylsulfonic acids (sulfonic acids with straight-chain or branched alkyl radical having 1 to 20 carbon atoms), arylsulfonic acids or -disulfonic acids (aromatic radicals such as phenyl and naphthyl which carry one or two sulfonic acid groups), alkylphosphonic acids (phosphonic acids with straight-chain or branched alkyl radicals having 1 to 20 carbon atoms), arylphosphonic acids or -diphosphonic acids (aromatic radicals such as phenyl and naphthyl which carry one or two phosphoric acid radicals), where the alkyl and aryl radicals can carry further substituents, e.g. p-toluenesulfonic acid, salicylic acid, p-aminosalicylic acid, 2-phenoxybenzoic acid, 2-acetoxybenzoic acid etc.

Suitable metal ions are in particular ions of the elements of the first to eighth subgroup, especially chromium, manganese, iron, cobalt, nickel, copper, zinc, and in addition of the second main group, especially calcium and magnesium, and of the third and fourth main group, in particular aluminum, tin and lead. The metals can in this case optionally be present in various valences befitting them.

Suitable copper-containing fungicidal active compounds (II) are in general the known commercially available fungicides. Those which are particularly suitable are copper-containing fungicides from the group consisting of copper hydroxide, copper oxide, copper oxychloride sulfate, copper sulfate, oxine-copper, copper bis(3-phenylsalicylate), copper dihydrazinium disulfate, dicopper chloride trihydroxide and tricopper dichloride dimethyldithiocarbamate.

The pure active compounds I and II are preferably employed in the preparation of the mixtures, to which can be admixed further active compounds against harmful fungi or against other pests such as insects, arachnids or nematodes or alternatively herbicidal or growth-regulating active compounds or fertilizers.

The mixtures of the compounds I and II and the compounds I and II applied simultaneously, jointly or separately are distinguished by an outstanding action against a broad spectrum of phytopathogenic fungi, in particular from the Ascomycetes, Basidiomycetes, Phycomycetes and Deuteromycetes classes. In some cases they are systemically active and can therefore be employed as foliar and soil fungicides.

They have particular importance for the control of a multiplicity of fungi on various crop plants such as cotton, vegetable plants (e.g. cucumbers, beans, tomatoes, potatoes and cucurbits), barley, grass, oats, bananas, coffee, corn, fruit plants, rice, rye, soybeans, grapes, wheat, decorative plants, sugar cane and also on a large number of seeds.

In particular, they are suitable for the control of the following phytopathogenic fungi: *Erysiphe graminis* (powdery mildew) on cereals, *Erysiphe cichoracearum* and *Sphaerotheca fuliginea* on cucurbits, *Podosphaera leucotricha* on apples, Uncinula necator on vines, Puccinia species on cereals, Rhizoctonia species on cotton, rice and lawns, Ustilago species on cereals and sugar cane, venturia inaequalis (scab) on apples, Helminthosporium species on cereals, *Septoria nodorum* on wheat, *Botrytis cinerea* (gray mold) on strawberries, vegetables decorative plants and vines, *Cercospora arachidicola* on ground nuts, *Pseudocercosporella herpotrichoides* on wheat and barley, *Pyricularia oryzae* on rice, *Phytophthora infestans* on potatoes and tomatoes, *Plasmopara viticola* on vines, Pseudoperonospora species in hops and cucumbers, Alternaria species on vegetables and fruit, Mycosphaerella species in bananas and also Fusarium and Verticillium species.

They can moreover be used in the protection of materials (e.g. wood preservation), for example against *Paecilomyces variotii*.

The compounds I and II can be applied simultaneously, to be precise together or separately, or in succession, the sequence in the case of separate application in general having no effect on the control result.

The compounds I and II are customarily used in a weight ratio of 1:1 to 1:1000, preferably 1:1 to 1:100, in particular 1:3 to 1:10.

The application rates of the mixtures according to the invention are, especially in the case of agricultural cultivation areas, 0.01 to 5 kg/ha, preferably 0.05 to 3.5 kg/ha, in particular 0.1 to 2.0 kg/ha, depending on the type of effect desired.

The application rates here for the compounds I are 0.01 to 2.5 kg/ha, preferably 0.05 to 2.5 kg/ha, in particular 0.1 to 1.0 kg/ha.

The application rates for the compounds II are correspondingly 0.1 to 10 kg/ha, preferably 0.5 to 5 kg/ha, in particular 0.5 to 2.0 kg/ha.

In the treatment of seed, in general application rates of mixture of 0.001 to 250 g/kg of seed, preferably 0.01 to 100 g/kg, in particular 0.01 to 50 g/kg, are used.

If harmful fungi which are pathogenic to plants are to be controlled, the separate or joint application of the compounds I and II or of the mixtures of the compounds I and II is carried out by spraying or dusting the seeds, the plants or the soil before or after the sowing of the plants or before or after the emergence of the plants.

The novel fungicidal synergistic mixtures or the compounds I and II can be prepared, for example, in the form of directly sprayable solutions, powders and suspensions or in the form of high-percentage aqueous, oily or other suspensions, dispersions, emulsions, oil dispersions, pastes, dusts, broadcasting agents or granules and can be applied by spraying, atomizing, dusting, scattering or watering. The application form is dependent on the intended use; in each case it should guarantee a dispersion of the mixture according to the invention which is as fine and uniform as possible.

The formulations are prepared in a manner known per se, e.g. by addition of solvents and/or carriers. Inert additives such as emulsifiers or dispersants are customarily admixed to the formulations.

Suitable surface-active substances are the alkali metal, alkaline earth metal or ammonium salts of aromatic sulfonic acids, e.g. ligno-, phenol-, naphthalene- and dibutylnaphthalenesulfonic acid, and of fatty acids, alkyl- and alkylarylsulfonates, alkyl, lauryl ether and fatty alcohol sulfates, and also salts of sulfated hexa-, hepta- and octadecanols or fatty alcohol glycol ethers, condensation products of sulfonated naphthalene and its derivatives with formaldehyde, condensation products of naphthalene or of the naphthalenesulfonic acids with phenol and formaldehyde, polyoxyethylene octylphenyl ethers, ethoxylated isooctyl-, octyl- or nonylphenol, alkylphenyl or tributylphenyl polyglycol ethers, alkylaryl polyether alcohols, isotridecyl alcohol, fatty alcohol-ethylene oxide condensates, ethoxylated castor oil, polyoxyethylene or polyoxypropylene alkyl ethers, lauryl alcohol polyglycol ether acetate, sorbitol esters, lignin-sulfite waste liquors or methylcellulose.

Powders, broadcasting agents and dusts can be prepared by mixing or joint grinding of the compounds I or II or of the mixture of the compounds I and II with a solid carrier.

Granules (e.g. coated, impregnated or homogeneous granules) are customarily prepared by binding the active compound or the active compounds to a solid carrier.

Fillers or solid carriers used are, for example, mineral earths such as silica gel, silicic acids, silicates, talc, kaolin, limestone, lime, chalk, bole, loess, clay, dolomite, diatomaceous earth, calcium sulfate and magnesium sulfate, magnesium oxide, ground synthetic materials, and fertilizers such as ammonium sulfate, ammonium phosphate, ammonium nitrate, ureas and vegetable products such as cereal meal, tree bark meal, wood meal and nutshell meal, cellulose powder or other solid carriers.

The formulations in general contain from 0.1 to 95% by weight, preferably 0.5 to 90% by weight, of one of the compounds I or II or of the mixture of the compounds I and II. The active compounds are in this case employed in a purity of 90% to 100%, preferably 95% to 100% (according to NMR spectrum or HPLC).

The application of the compounds I or II, of the mixtures or of the corresponding formulations is carried out such that the harmful fungi, their habitat or the plants, seeds, soil, areas, materials or spaces to kept free from them are treated with a fungicidally active amount of the mixture, or of the compounds I and II in the case of separate application.

Application can be carried out before or after the attack by the harmful fungi.

USE EXAMPLE

The synergistic action of the mixtures according to the invention could be shown by the following tests:

The active compounds were prepared separately or jointly as a 10% strength emulsion in a mixture of 63% by weight of cyclohexanone and 27% by weight of emulsifier and diluted with water according to the desired concentration.

Action against *Phytophthora infestans* (tomato blight)

Leaves of pot plants of the variety "Große Fleischtomate" were sprayed until dripping wet with an aqueous suspension which had been prepared from a stock solution of 10% of active compound, 63% of cyclohexanone and 27% of emulsifier. On the following day, the leaves were infected with an aqueous zoospore suspension of *Phytophthora infestans*. The plants were then placed in a water vapor-saturated chamber at temperatures between 16 and 18° C. After 6 days, the tomato blight had developed so severely on the untreated, but infected control plants that the attack could be determined visually in %.

Evaluation was carried out by determination of the attacked leaf areas in percent. These percentage values were converted into efficiencies. The efficiency (W) was determined according to the Abbot formula as follows:

$$W = (1-\alpha\beta) \cdot 100$$

α corresponds to the fungal attack on the treated parts in % and

β corresponds to the fungal attack on the untreated (control) plants in %

At an efficiency of 0, the attack on the treated plants corresponds to that on the untreated control plants; at an efficiency of 100 the treated plants exhibited no attack.

The efficiencies of the active compound mixtures to be expected were determined according to the Colby formula [R. S. Colby, Weeds 15, 20–22 (1967)] and compared with the observed efficiencies.

$$E = x+y-x\cdot y/100 \qquad \text{Colby formula}$$

E is the efficiency to be expected, expressed in % of the untreated control, on use of the mixture of the active compounds A and B in the concentrations a and b x is the efficiency, expressed in % of the untreated control, on use of the active compound A in the concentration a is the efficiency, expressed in % of the untreated control, on use of the active compound B in the concentration b The results can be seen in the following Tables 2 and 3.

| Ex. | Active compound | Active compound concentration in the spray liquor in ppm | Efficiency in % of the untreated control |
|---|---|---|---|
| 1V | Control (untreated) | (100% attack) | 0 |
| 2V | Compound I.32 | 2 | 80 |
|  |  | 1 | 30 |
|  |  | 0.5 | 30 |
|  |  | 0.25 | 0 |
| 3V | II.1 = Cuproxate tribasic copper sulfate | 100 | 10 |
|  |  | 50 | 0 |
|  |  | 25 | 0 |
|  |  | 12.5 | 0 |

TABLE 3

| Ex. | Mixtures according to the invention | Observed efficiency | Calculated efficiency*) |
|---|---|---|---|
| 4 | 1 ppm I.32 + 100 ppm II.1 (Mixture 1:100) | 95 | 37 |
| 5 | 0.5 ppm I.32 + 50 ppm II.1 (Mixture 1:100) | 80 | 30 |
| 6 | 0.25 ppm I.32 + 25 ppm II.1 (Mixture 1:100) | 50 | 0 |
| 7 | 2 ppm I.32 + 100 ppm II.1 (Mixture 1:50) | 97 | 82 |
| 8 | 1 ppm I.32 + 50 ppm II.1 (Mixture 1:50) | 95 | 30 |
| 9 | 0.5 ppm I.32 + 25 ppm II.1 (Mixture 1:50) | 93 | 30 |
| 10 | 2 ppm I.32 + 50 ppm II.1 (Mixture 1:25) | 100 | 80 |
| 11 | 1 ppm I.32 + 25 ppm II.1 (Mixture 1:25) | 97 | 30 |
| 12 | 0.5 ppm I.32 + 12.5 ppm II.1 (Mixture 1:25) | 97 | 30 |

*) calculated according to the Colby formula

It emerges from the results of the test that the observed efficiency in all mixing ratios is higher than the efficiency precalculated according to the Colby formula.

$$W = (1-\alpha/\beta) \cdot 100$$

Use Example 2—Activity against Phytophthora infestans on tomatoes

Leaves of pot plants of the variety "Große Fleischtomate St. Pierre" were sprayed until dripping wet with an aqueous suspension which was prepared from a stock solution of 10% of active compound, 63% of cyclohexanone and 27% of emulsifier. On the following day, the leaves were infected with a cold aqueous zoospore suspension of Phytophthora infestans having a density of $0.25 \times 10^6$ spores/ml. The plants were then placed in a water vapor-saturated chamber at temperatures between 18 and 20° C. After 6 days, the tomato blight had developed so severely on the untreated, but infected control plants that the attack could be determined visually in %.

The visually determined values for the percentage proportion of attacked leaf areas were converted into efficiencies as % of the untreated control. Efficiency 0 is the same attack as in the untreated control, efficiency 100 is 0% attack. The efficiencies to be expected for active compound combinations were determined according to the Colby formula (Colby, S. R. (Calculating synergistic and antagonistic responses of herbicide Combinations", Weeds, 15, pp. 20–22, 1967) and compared with the observed efficiencies.

As component II, tribasic copper sulfate $3Cu(OH)_2 \cdot xCuSO_4$ (commercially obtainable under the tradename Cuproxat) was employed.

The results of the tests can be seen from Tables 4 and 5 below:

TABLE 4

| Ex. | Active compound | Conc. in ppm | Efficiency in % of the untreated control |
|---|---|---|---|
| 13V | without | (87% attack) | 0 |
| 14V | Compound I.23 | 2 | 8 |
|  |  | 1 | 0 |
|  |  | 0.5 | 0 |
|  |  | 0.25 | 8 |
|  |  | 0.125 | 0 |
| 15V | Compound I.38 | 2 | 0 |
|  |  | 1 | 0 |
|  |  | 0.5 | 8 |
| 16V | Compound II | 200 | 8 |
|  |  | 100 | 8 |
|  |  | 50 | 8 |
|  |  | 25 | 8 |
|  |  | 12.5 | 0 |

TABLE 5

| Ex. | Mixture according to the invention (conc. in ppm) | Observed efficiency | Calculated efficiency* |
|---|---|---|---|
| 17 | 2 ppm I.23 + 200 ppm II | 54 | 15 |
| 18 | 1 ppm I.23 + 100 ppm II | 42 | 8 |
| 19 | 0.125 ppm I.23 + 12.5 ppm II | 31 | 0 |
| 20 | 2 ppm I.23 + 100 ppm II | 31 | 15 |
| 21 | 2 ppm I.38 + 200 ppm II | 77 | 8 |
| 22 | 1 ppm I.38 + 100 ppm II | 42 | 8 |
| 23 | 2 ppm I.38 + 100 ppm II | 77 | 8 |
| 24 | 1 ppm I.38 + 50 ppm II | 31 | 8 |
| 25 | 2 ppm I.38 + 50 ppm II | 65 | 8 |
| 26 | 1 ppm I.38 + 25 ppm II | 54 | 8 |

TABLE 5-continued

| Ex. | Mixture according to the invention (conc. in ppm) | Observed efficiency | Calculated efficiency* |
|---|---|---|---|
| 27 | 0.5 ppm I.38 + 12.5 ppm II | 29 | 8 |

*calculated according to the Colby formula

It emerges from the results of the experiments that the observed efficiency in all mixing ratios is higher than the efficiency precalculated according to the Colby formula.

What is claimed is:

1. A fungicidal composition comprising
   a.1) a carbamate compound of formula I

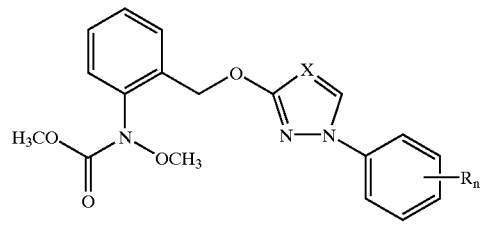

in which X is CH or N, n is 0, 1 or 2 and R is halogen, $C_1$–$C_4$-alkyl or $C_1$–$C_4$-haloalkyl, where the radicals R are identical or different when n is 2, and
   b) a copper-containing fungicidal active compound (II) as active components, wherein the active components are present in synergistically effective amounts.

2. The composition defined in claim 1, wherein the compound of formula I or a salt or adduct thereof and the compound (II) are present in a weight ratio of from 1:1 to 1:1000.

3. The composition defined in claim 1, which is packaged in two parts, one part containing the compound of formula I in a solid or liquid carrier and the other part containing the compound (II) in a solid or liquid carrier.

4. The composition defined claim 1, wherein the compound (II) is selected from the group consisting of copper hydroxide, copper oxide, copper oxychloride sulfate, copper sulfate, oxine-copper, copper bis(3-phenylsalicylate), copper dihydrazinium disulfate, dicopper chloride trihydroxide and tricopper dichloride dimethyldithiocarbamate.

5. A process for controlling harmful fungi, which comprises treating the harmful fungi, their habitat or plants, seeds, soil, areas, materials or spaces to be kept free from with synergistically effective amounts of the compound of formula I defined in claim 1 or a salt or adduct thereof and the compound (II) defined in claim 1.

6. The process of claim 5, wherein the compound of formula I or the salt or adduct thereof and the compound (II) are applied jointly or separately simultaneously or in succession.

7. The process of claim 5, wherein the compound I of formula I or the salt or adduct thereof is applied in an amount from 0.01 to 2.5 kg/ha.

8. The process of claim 5, wherein the compound (II) is applied in an amount from 0.1 to 10 kg/ha.

9. The method of claim 5, wherein the compound (II) is selected from the group consisting of copper hydroxide, copper oxide, copper oxychloride sulfate, copper sulfate, oxine-copper, copper bis(3-phenylsalicylate), copper dihydrazinium disulfate, dicopper chloride trihydroxide and tricopper dichloride dimethyldithiocarbamate.

* * * * *